United States Patent
Sarr

(10) Patent No.: US 7,430,913 B2
(45) Date of Patent: *Oct. 7, 2008

(54) RAPID PROTOTYPE INTEGRATED MATRIX ULTRASONIC TRANSDUCER ARRAY INSPECTION APPARATUS, SYSTEMS, AND METHODS

(75) Inventor: Dennis P. Sarr, Kent, WA (US)

(73) Assignee: The Boeing Company, Chicago, IL (US)

( * ) Notice: Subject to any disclaimer, the term of this patent is extended or adjusted under 35 U.S.C. 154(b) by 386 days.

This patent is subject to a terminal disclaimer.

(21) Appl. No.: 11/213,651

(22) Filed: Aug. 26, 2005

(65) Prior Publication Data

US 2007/0044562 A1    Mar. 1, 2007

(51) Int. Cl.
G01N 29/04    (2006.01)
(52) U.S. Cl. .............................. 73/618; 73/628; 73/641; 73/644
(58) Field of Classification Search .................... 73/618, 73/626, 628, 640, 641, 644
See application file for complete search history.

(56) References Cited

U.S. PATENT DOCUMENTS

| | | | |
|---|---|---|---|
| 3,958,451 A | 5/1976 | Richardson | |
| 4,774,842 A | 10/1988 | Kollar | |
| 5,007,291 A * | 4/1991 | Walters et al. ................ | 73/640 |
| 5,050,703 A | 9/1991 | Graff et al. | |
| 5,148,414 A | 9/1992 | Graff et al. | |
| 5,164,921 A | 11/1992 | Graff et al. | |
| 5,421,203 A | 6/1995 | Graff et al. | |
| 5,535,628 A * | 7/1996 | Rutherford .................... | 73/622 |
| 5,567,881 A * | 10/1996 | Myers ......................... | 73/629 |
| 5,585,564 A | 12/1996 | Brunty et al. | |
| 5,677,490 A | 10/1997 | Gunther et al. | |
| 6,516,668 B2 | 2/2003 | Havira et al. | |
| 6,641,535 B2 * | 11/2003 | Buschke et al. ............. | 600/437 |
| 6,722,202 B1 | 4/2004 | Kennedy et al. | |
| 6,772,635 B1 * | 8/2004 | Sale et al. ..................... | 73/622 |
| 6,829,959 B2 * | 12/2004 | Gifford et al. .............. | 73/866.5 |

(Continued)

FOREIGN PATENT DOCUMENTS

DE    198 26 759 C1    12/1999

OTHER PUBLICATIONS

U.S. Appl. No. 10/943,088, filed Sep. 16, 2004; Inventors: Georgeson, entitled *Magnetically Attracted Inspecting Apparatus and Method Using a Ball Bearing*.

(Continued)

*Primary Examiner*—Hezron E. Williams
*Assistant Examiner*—Jacques M. Saint-Surin
(74) *Attorney, Agent, or Firm*—Alston & Bird LLP

(57) ABSTRACT

Apparatus, systems, and methods for inspecting a structure are provided which use a sensor holder constructed from rapid prototyping, such as stereolithography, and which is configured to support a plurality of inspection sensors typically arranged in an ordered matrix array and possibly with one or more additional inspection sensors aligned for inspection of difficult to inspect features of a structure such as radius corner or edge features. Rapid prototype integrated matrix array inspection apparatus, systems, and methods provide fast and efficient methods of constructing custom inspection devices.

27 Claims, 4 Drawing Sheets

U.S. PATENT DOCUMENTS

| | | | |
|---|---|---|---|
| 6,843,131 B2 | 1/2005 | Graff et al. | |
| 6,931,931 B2 | 8/2005 | Graff et al. | |
| 7,064,332 B2 * | 6/2006 | Favro et al. | 250/341.6 |
| 7,249,512 B2 * | 7/2007 | Kennedy et al. | 73/618 |
| 7,253,908 B2 * | 8/2007 | Vaccaro et al. | 356/607 |
| 7,263,889 B2 * | 9/2007 | Kennedy et al. | 73/620 |
| 2004/0237653 A1 | 12/2004 | Graff et al. | |
| 2006/0243051 A1 * | 11/2006 | Bui et al. | 73/618 |
| 2007/0044563 A1 * | 3/2007 | Sarr et al. | 73/618 |
| 2007/0044564 A1 * | 3/2007 | Bui et al. | 73/618 |

OTHER PUBLICATIONS

U.S. Appl. No. 10/943,135, filed Sep. 16, 2004; Inventors: Georgeson, entitled *Magnetically Attracted Inspecting Apparatus and Method Using a Fluid Bearing*.

U.S. Appl. No. 11/041,499, filed Jan. 24, 2005; Inventors: Kennedy, entitled *Non-Destructive Stringer Inspection Apparatus and Method*.

Stereolithography Made Easy, *What is Rapid Prototyping?*, available at http://www.stereolithography.com/rapidprototyping.php, May 23, 2005, 11 pages.

* cited by examiner

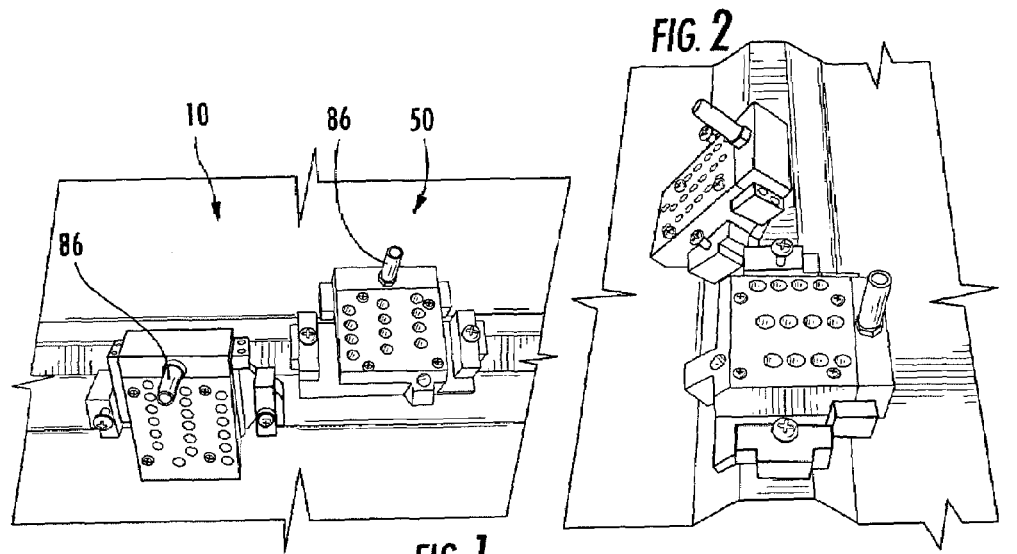
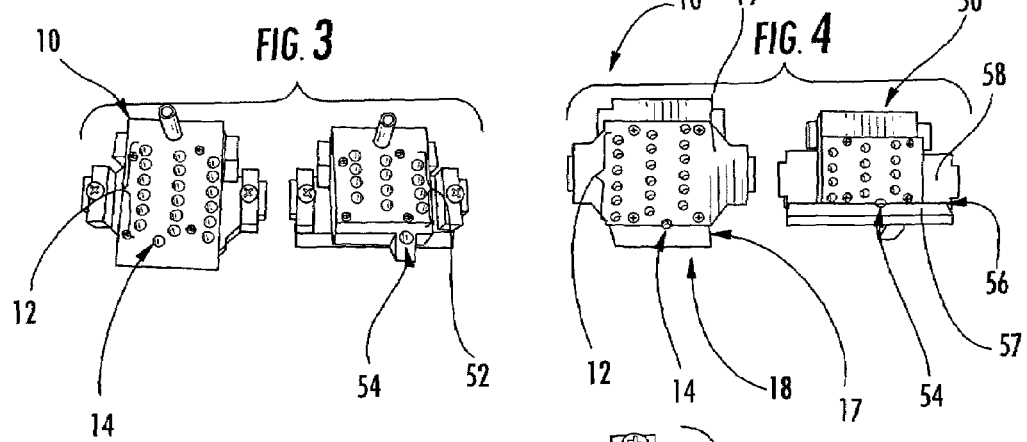
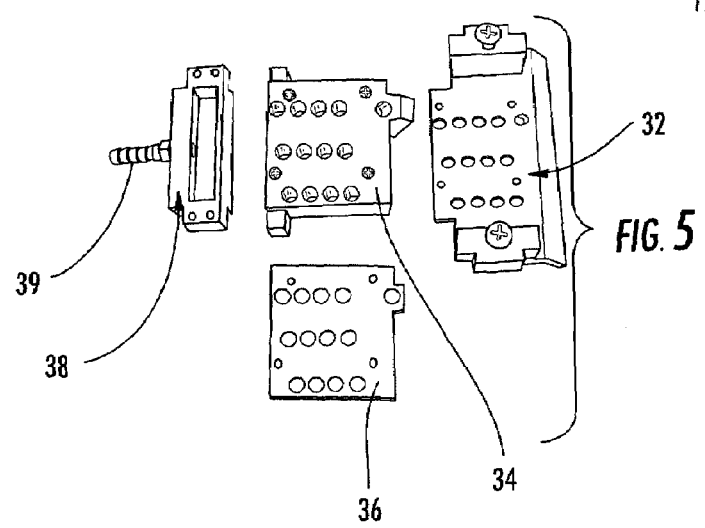

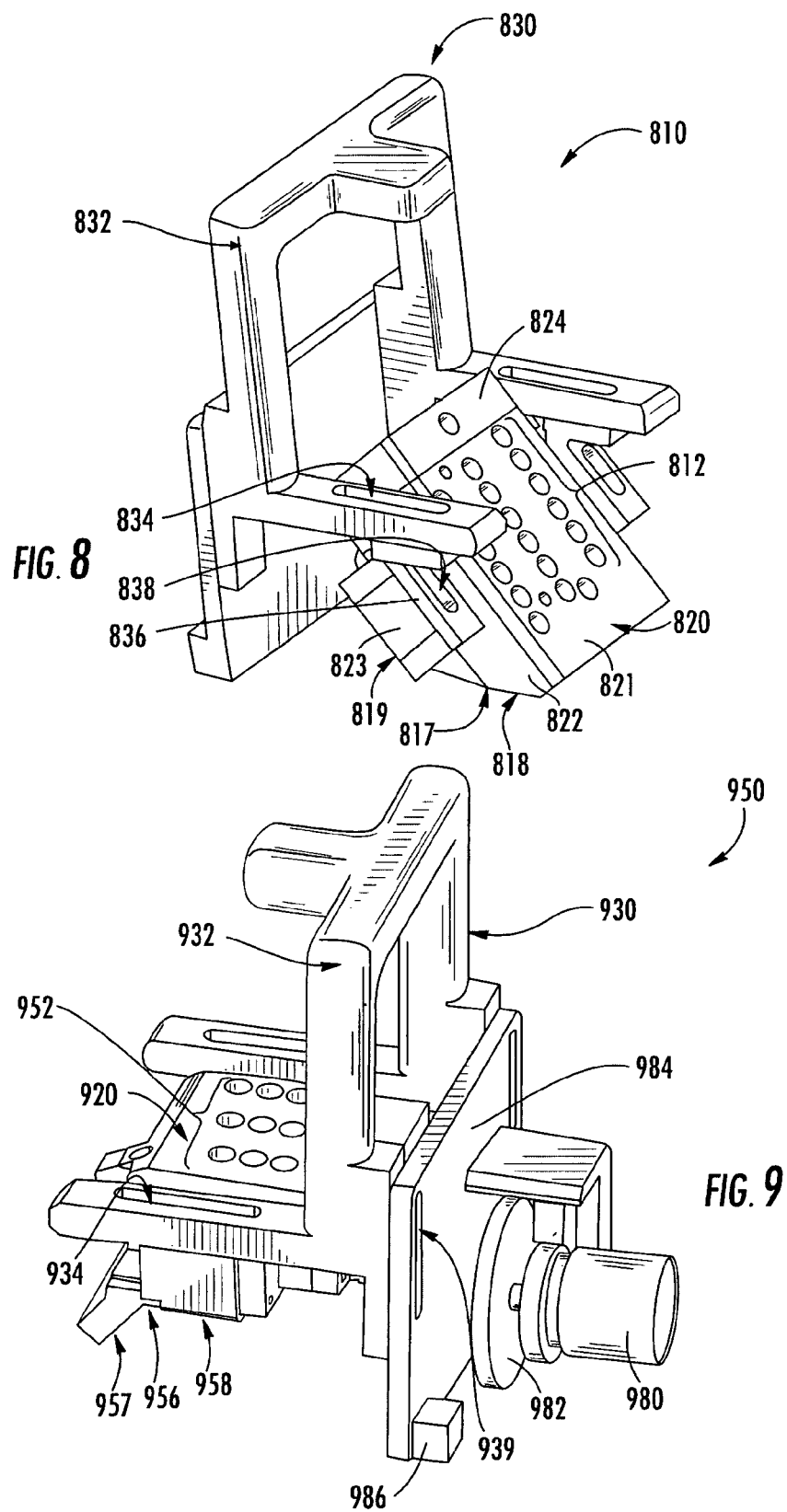

RAPID PROTOTYPE INTEGRATED MATRIX ULTRASONIC TRANSDUCER ARRAY INSPECTION APPARATUS, SYSTEMS, AND METHODS

CROSS-REFERENCE TO RELATED APPLICATIONS

The contents of U.S. Pat. No. 6,722,202; application Ser. No. 10/943,088, entitled "Magnetically Attracted Inspecting Apparatus and Method Using a Ball Bearing," filed Sep. 16, 2004; application Ser. No. 10/943,135, entitled "Magnetically Attracted Inspecting Apparatus and Method Using a Fluid Bearing," filed Sep. 16, 2004; and application Ser. No. 11/041,499, entitled "Non-Destructive Stringer Inspection Apparatus and Method," filed Jan. 24, 2005, are incorporated herein by reference in their entireties.

FIELD OF THE INVENTION

The present invention relates generally to an apparatus and method for inspecting a structure and, more particularly, embodiments of the present invention relate to apparatus, systems, and methods for non-destructive inspection of a structure using a rapid prototype integrated matrix pulse echo ultrasonic transducer array.

BACKGROUND

Non-destructive inspection (NDI) of structures involves thoroughly examining a structure without harming the structure or requiring significant disassembly of the structure. Non-destructive inspection is typically preferred to avoid the schedule, labor, and costs associated with removal of a part for inspection, as well as avoidance of the potential for damaging the structure. Non-destructive inspection is advantageous for many applications in which a thorough inspection of the exterior and/or interior of a structure is required. For example, non-destructive inspection is commonly used in the aircraft industry to inspect aircraft structures for any type of internal or external damage to or defects (flaws) in the structure. Inspection may be performed during manufacturing of a structure or after the completed structure has been put into service, including field testing, to validate the integrity and fitness of the structure during manufacturing and ongoing and future use while in-service.

Among the structures that are routinely non-destructively tested are composite structures, such as composite sandwich structures and other adhesively bonded panels and assemblies and structures with contoured surfaces, such as hat stringers or hat stiffeners made from carbon fiber reinforced and graphite epoxy (Gr/Ep) materials and co-cured or co-bonded hat stringers. These composite structures, and a shift toward lightweight composite and bonded materials such as using graphite materials, dictate that devices and processes are available to ensure structural integrity, production quality, and life-cycle support for safe and reliable use. As such, it is frequently desirable to inspect structures to identify any defects, such as cracks, discontinuities, voids, or porosity, which could adversely affect the performance of the structure. For example, typical defects in composite sandwich structures, generally made of one or more layers of lightweight honeycomb or foam core material with composite or metal skins bonded to each side of the core, include disbonds which occur at the interfaces between the core and the skin or between the core and a buried septum.

Various types of sensors may be used to perform non-destructive inspection. One or more sensors may move over the portion of the structure to be examined, and receive data regarding the structure. For example, a pulse-echo (PE), through transmission (TT), or shear wave sensor may be used to obtain ultrasonic data, such as for thickness gauging, detection of laminar defects and porosity, and/or crack detection in the structure. Resonance, pulse echo, or impedance sensors may be used to provide indications of voids or porosity, such as in adhesive bondlines of the structure. High resolution inspection of an aircraft structure is commonly performed using semi-automated ultrasonic testing (UT) to provide a plan view image of the part or structure under inspection. While solid laminates and some composite structures are commonly inspected using one-sided pulse echo ultrasonic (PEU) testing, composite sandwich structures are commonly inspected using through-transmission ultrasonic (TTU) testing for high resolution inspection. In pulse echo ultrasonic (PEU) testing, ultrasonic sensors, such as ultrasonic transducers, are positioned adjacent to or near one surface of the structure to be inspected. For example, the PEU transducer transmits an ultrasonic signal into the structure under inspection and receives the reflection of the ultrasonic signal from the structure. In through-transmission ultrasonic inspection, ultrasonic sensors such as transducers, or a transducer and a receiver sensor, are positioned facing the other but contacting opposite sides of the structure. An ultrasonic signal is transmitted by at least one transducer, propagated through the structure, and received by the other transducer. Data acquired by sensors is typically processed and then presented to a user via a display as a graph of amplitude of the received signal. A data acquisition board and data handling software may be used for collection and display of inspection data, such as displaying the data on a computer monitor as an image representation of the structure under inspection, such as a hat stringer, supplemented with corresponding color and/or graphical data of the inspection to permit examination by a qualified inspector.

Non-destructive ultrasonic testing often involves coupling an ultrasonic signal from a transducer or transducer array to the surface of the structure under inspection, such as bubbling water between an inspection device and the structure. While solid laminates may be inspected using one-sided pulse echo ultrasonic (PEU) testing and bondline thickness may be measured using one-sided pulse echo ultrasonic testing, composite sandwich structures typically require through-transmission ultrasonic (TTU) testing for high resolution inspection. In through-transmission ultrasonic inspection, ultrasonic sensors such as transducers, or a transducer and a receiver sensor, are positioned facing the other but contacting opposite sides of the structure to be inspected such as opposite surfaces of a composite material. An ultrasonic signal is transmitted by at least one of the transducers, propagated through the structure, and received by the other transducer. Data acquired by sensors, such as PEU and TTU transducers, is typically processed by a processing element, and the processed data may be presented to a user via a display.

Non-destructive inspection may be performed manually by technicians who move an appropriate sensor over the structure. Manual scanning generally consists of a trained technician holding a sensor and moving the sensor along the structure to ensure the sensor is capable of testing all desired portions of the structure. In many situations, the technician must repeatedly move the sensor side-to-side in one direction while simultaneously indexing the sensor in another direction. For a technician standing beside a structure, the technician may repeatedly move the sensor right and left, and back again, while indexing the sensor between each pass. In addition, because the sensors typically do not associate location information with the acquired data, the same technician who is manually scanning the structure must also watch the sensor display while scanning the structure to determine where the defects, if any, are located in the structure. The quality of the inspection, therefore, depends in large part upon the technician's performance, not only regarding the motion of the sensor, but also the attentiveness of the technician in interpreting the displayed data.

Semi-automated inspection systems have been developed to overcome some of the shortcomings with manual inspection techniques. For example, the Mobile Automated Scanner (MAUS®) system is a mobile scanning system that generally employs a fixed frame and one or more automated scanning heads typically adapted for ultrasonic inspection. A MAUS system may be used with pulse-echo, shear wave, and through-transmission sensors. The fixed frame may be attached to a surface of a structure to be inspected by vacuum suction cups, magnets, or like affixation methods. Smaller MAUS systems may be portable units manually moved over the surface of a structure by a technician. However, for through-transmission ultrasonic inspection, a semi-automated inspection system requires access to both sides of a structure which, at least in some circumstances, will be problematic, if not impossible, particularly for semi-automated systems that use a fixed frame for control of automated scan heads.

Automated inspection systems have also been developed as an alternative to manual and semi-automated inspection techniques. For single sided inspection methods, such as pulse echo ultrasonic inspection, a single-arm robotic device, such as an R-200iA™ series six-axis robot from FANUC Robotics of Rochester Hills, Mich., or an IRB 6600 robot from ABB Ltd. of Zurich, Switzerland, may be used to position and move a pulse echo ultrasonic inspection device. For through transmission inspection, a device such as the Automated Ultrasonic Scanning System (AUSS®) system may be used. The AUSS system has two robotically controlled probe arms that can be positioned proximate the opposed surfaces of the structure undergoing inspection with one probe arm moving an ultrasonic transmitter along one surface of the structure, and the other probe arm correspondingly moving an ultrasonic receiver along the opposed surface of the structure. Conventional automated scanning systems, such as the AUSS-X system, therefore require access to both sides of a structure for through transmission inspection which, at least in some circumstances, will be problematic, if not impossible, particularly for very large or small structures. To maintain the transmitter and receiver in proper alignment and spacing with one another and with the structure undergoing inspection, the AUSS-X system has a complex positioning system that provides motion control in ten axes. The AUSS system can also perform pulse echo inspections, and simultaneous dual frequency inspections.

To increase the rate at which the inspection of a structure is conducted, a scanning system may include arrays of inspection sensors, i.e., arrays of transmitters and/or detectors. As such, the inspection of the structure can proceed more rapidly and efficiently, thereby reducing the costs associated with the inspection. However, typically each structure and inspection application requires a corresponding array designed to provide transducer alignment (position and orientation with respect to the surface(s) of the structure) and scan coverage for the structure. Conventionally, special inspection devices are constructed for scanning different structures and different sizes and configurations of structures. Designing an inspection device using an array of inspection sensors for scanning a particular structure requires ensuring proper alignment of the inspection sensors with respect to the surface(s) of the structure and ensuring scan coverage of the structure. For example, consideration must be taken for flat and curved surfaces as well as features of the structure, including radius features such as convex edges and concave corners. Constructing specialized inspection devices for each inspection application conventionally has required significant time and financial and human resources to design and build these specialized inspection devices. Also, conventionally, each specialized inspection device is designed for and capable of only inspecting one structure, and typically cannot adjust for different sizes of the structure or different inspection applications that use different array sizes.

Accordingly, a need exists for improved non-destructive inspection apparatus, systems, and methods for inspecting a structure, particularly for using an array of inspection sensors for inspecting structures with multiple sides and/or difficult to inspect features such as corners.

SUMMARY OF THE INVENTION

Improved apparatus, systems, and methods for inspecting a structure, such as inspecting structures with multiple sides and/or difficult to inspect features using an array of inspection sensors, are provided which use a sensor holder constructed from rapid prototyping, such as stereolithography, and which is configured to support a plurality of inspection sensors typically arranged in a matrix array and possibly with one or more additional inspection sensors aligned for inspection of difficult to inspect features of a structure such as corners and edges. Embodiments of methods of the present invention provide fast and efficient methods of constructing custom inspection devices for inspecting structures with an array of inspection sensors.

According to another aspect of the present invention, to facilitate coupling of ultrasonic signals between inspection sensors of apparatus and systems of embodiments of the present invention, such as pulse echo ultrasonic sensors, a couplant may be disposed between the inspection sensors and a respective surface of the structure under inspection. An apparatus of an embodiment of an inspection device according to the present invention may advantageously include a fluid manifold capable of feeding a fluid couplant into a central cavity of the apparatus that permits the fluid couplant to flow to one or more of the positions where inspection sensors are disposed in the inspection device to couple ultrasonic signals of the inspection sensors to a surface of the structure.

According to another aspect of the present invention, a method for constructing custom inspection devices for inspecting structures with an array of inspection sensors is provided, such as inspection devices configured to support a matrix array of inspection sensors and possibly with one or more additional inspection sensors aligned for inspection of difficult to inspect features of a structure such as corners and edges.

These and other characteristics, as well as additional details, of the present invention are further described in the Detailed Description with reference to these and other embodiments.

BRIEF DESCRIPTION OF THE DRAWING(S)

Having thus described the invention in general terms, reference will now be made to the accompanying drawings, which are not necessarily drawn to scale, and wherein:

FIG. 1 is a perspective view of a pair of inspection devices of embodiments of the present invention for inspecting a hat stringer;

FIG. 2 is another view of the pair of inspection devices of FIG. 1;

FIG. 3 is a top plan view of the pair of inspection devices of FIG. 1;

FIG. 4 is a bottom plan view of the pair of inspection devices of FIG. 1;

FIG. 5 is a schematic diagram of the components for one of the inspection devices of FIG. 1;

FIG. 8 is a schematic diagram of an inspection device of yet another embodiment of the present invention for inspecting the sides of a hat stringer;

FIG. 9 is a schematic diagram of an inspection device of yet another embodiment of the present invention for inspecting the top of a hat stringer.

DETAILED DESCRIPTION

Figure 6:
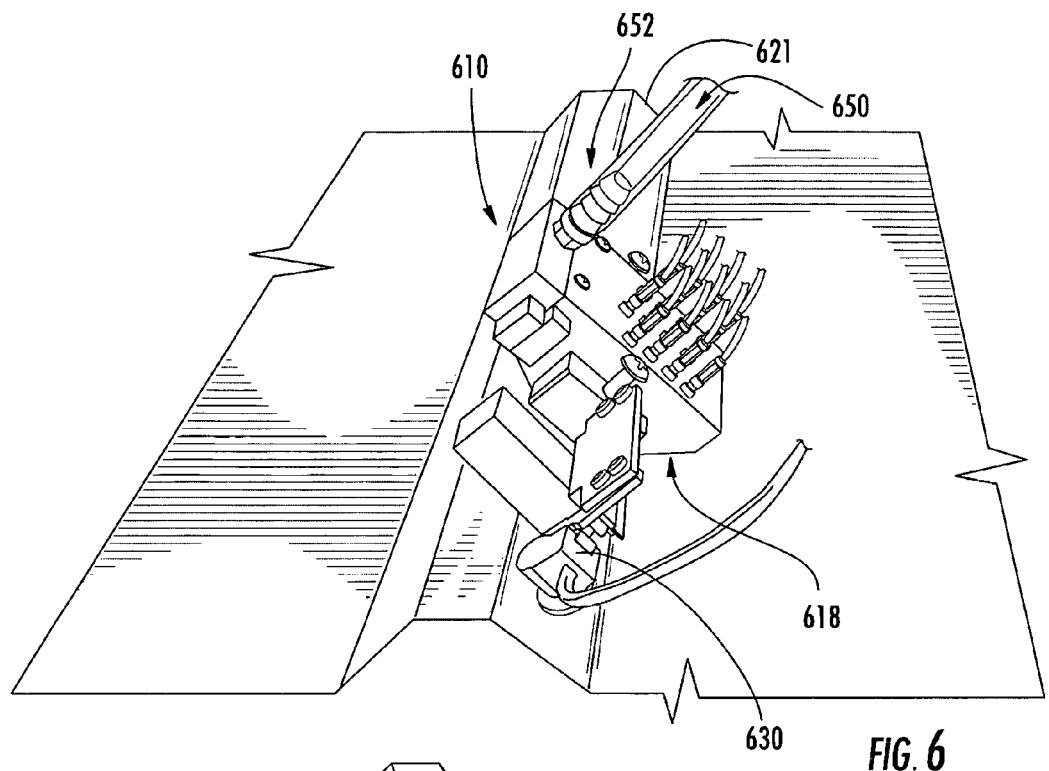
FIG. 6 is a perspective view of an inspection device of another embodiment of the present invention for inspecting the sides of a hat stringer.

The present invention will be described more fully with reference to the accompanying drawings. Some, but not all, embodiments of the invention are shown. The invention may be embodied in many different forms and should not be construed as limited to the described embodiments. Like numbers and variables refer to like elements and parameters throughout the drawings.

While embodiments of the present invention are described herein with reference to pulse echo ultrasonic (PEU) non-destructive inspection and typically would be used with pulse echo ultrasonic non-destructive inspection, embodiments of the present invention are not limited to one-sided inspection methods such as pulse echo ultrasonic non-destructive inspection, and may be used for other inspection methods, including without limitation through transmission ultrasonic inspection. For example, inspection of hat stringers and other structures with complex configurations may be more easily inspected using an embodiment of the present invention employing a one sided inspection method such as pulse echo ultrasonic inspection; however, magnetically coupled inspection probes may use embodiments of the present invention for through transmission ultrasonic inspection.

Embodiments of rapid prototype integrated matrix ultrasonic transducer array inspection apparatus, systems, and methods of the present invention are described herein with respect to inspection of hat stringers, especially composite hat stringers for an aircraft fuselage. However, the apparatus, systems, and methods may also be used for structures other than hat stringers and similar applications which require non-destructive inspection, including without limitation other composite structures with difficult-to-inspect geometric configurations and/or remote locations. Embodiments of apparatus, systems, and methods of the present invention may be used for manual hand scanning by a technician or using a semi-automatic or automatic robotic motion control system, possibly also using magnetic coupling such as described with reference to the magnetically coupled probes in co-pending application Ser. Nos. 10/943,088; 10/943,135; and 11/041, 499. One advantage of embodiments of the present invention is that rapid prototyping permits creation of inspection devices with custom shapes and custom sensor arrays for custom inspection applications according to the corresponding shapes and features of the structure to be inspected, such as the flat and curved features of a hat stringer. Accordingly, embodiments of apparatus and systems according to the invention may be designed and constructed to accommodate variations of structure shapes, sizes, and other characteristics, such as different hat stringer design shapes, sizes, and part thickness changes.

An embodiment of an apparatus according to the invention may be designed to have a surface-side (the portion of the apparatus proximate and/or riding on a structure under inspection) corresponding to the shape of at least a portion of the surface of the structure. For example, if the structure to be inspected has a concave shape, the surface-side of the apparatus may be designed to have a convex shape that fits the concave shape of the structure. Similarly, if the structure to be inspected is a hat stringer, the apparatus may be designed to correspond to the side web and hat shapes, sizes, and corner angles of the hat stringer. For example, an apparatus designed only to inspect one side web of a hat stringer and an adjacent attachment corner of the hat stringer where the hat stringer attaches to the superstructure, may be designed (shaped, sized, etc.) to conform to the structure, to support a matrix array of pulse echo transducers aligned to provide inspection coverage of the side web of the hat stringer, and to support a pulse echo transducer aligned to provide inspection coverage of the attachment corner of the hat stringer.

In addition to rapid prototyping allowing for custom shapes of embodiments of inspection devices of the present invention, embodiments of inspection devices of the present invention also allow for custom inspection sensor arrays by incorporating an integrated matrix ultrasonic transducer array, and/or structure thereof. For example, one embodiment of an inspection device of the present invention may include the structure to support an integrated matrix ultrasonic transducer array. Such a structure may include an n×m matrix of holes (sensor recesses), such as a 3-by-6 matrix of holes, with the n rows offset such that the m holes of each of the n rows are aligned to scan a structure along a different linear position than any of the other holes in the matrix. The integrated matrix also allows a custom inspection application to select which holes to use with transducers, and to plug or not use the other holes. Thus, an inspection device of an embodiment of the present invention with a 3×6 matrix can also be used, for example, for a 2×4 inspection application. A structure for supporting an array of transducers is referred to herein as a sensor holder.

Figure 7:
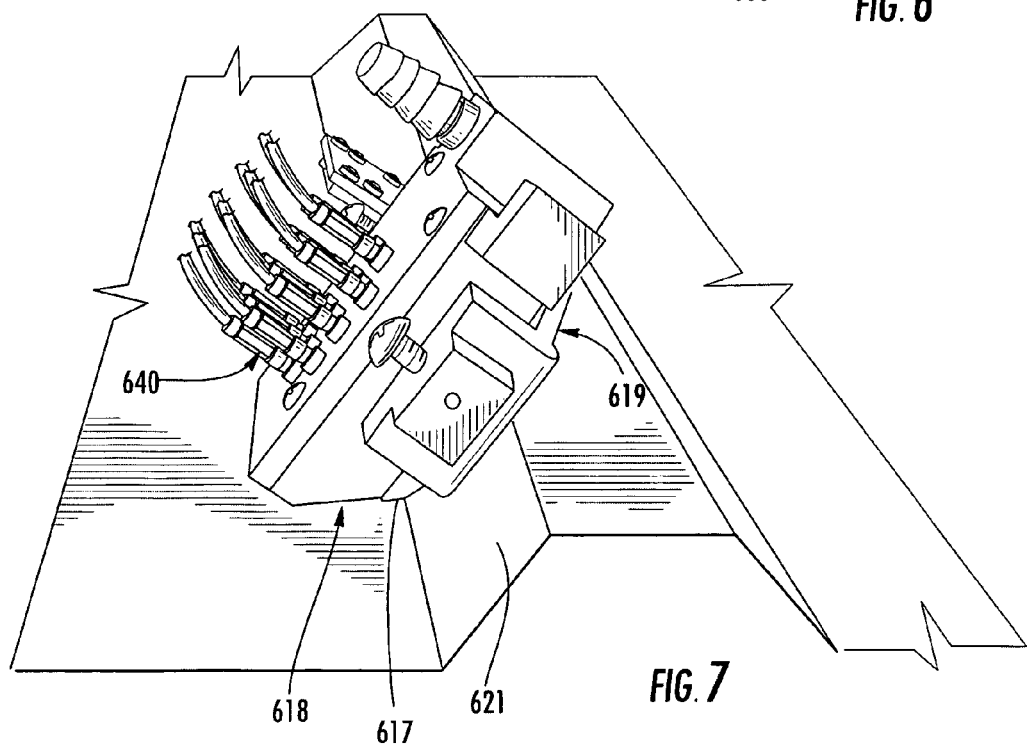
FIG. 7 is another view of the inspection device of FIG. 6.

FIGS. 1 and 2 show two inspection devices 10, 50 placed on a hat stringer as they might be used for an inspection operation. FIGS. 3 and 4 show the two inspection devices 10, 50 in more detail from a top plan view in FIG. 3 and a bottom plan view in FIG. 4: FIG. 5 is a schematic diagram of the components for the inspection device 50 designed for inspecting a cap top of a hat stringer. FIGS. 6 and 7 show an inspection device 610 in operation scanning the web side 621 of a hat stringer. The inspection device 610 of FIGS. 6 and 7 is nearly identical to the inspection device 10 of FIGS. 1-4; the sensor holders and fluid manifolds are the same, but the inspection device 610 of FIGS. 6 and 7 includes a linear encoder 630, a plurality of pulse echo ultrasonic sensors 640, and a fluid supply line 650 connected to a fluid inlet port 652.

Inspection devices, and particularly the sensor holders of inspection devices, of embodiments of the present invention are designed to correspond to the shape and size of structures to be inspected. For example, the inspection devices 10, 50, 610, 810, 950 depicted in FIGS. 1-9 are intended for inspection of hat stringers; some 10, 610, 810 for inspection of web sides of hat stringers; others 50, 950 for inspection of cap tops of hat stringers. For example, the inspection devices 10, 610, 810 each are designed with a flat, surface-side "skin" portion 18, 618, 818 designed for traveling over the structure skin or portion of the hat stringer attached to the structure skin. The inspection devices 10, 610, 810 each have a convex corner 17, 617, 817 corresponding to the corner of the hat stringer or between the hat stringer and the structure skin and transitioning to a flat, surface-side "web" portion 19, 619, 819. The angle between the skin portion 18, 618, 818 and web portion 19, 619, 819 correspond to the angle between the skin and the web of the hat stringer to permit the inspection device 10, 610, 810 to travel over the web side of the hat stringer. Similarly, the inspection devices 50, 650, 950 each are designed with a flat, surface-side "cap" portion 58, 658, 858 designed for traveling over the cap top of a hat stringer. The inspection devices 50, 650, 950 also include a concave corner 56, 656, 956 corresponding to the corner of the hat stringer between the web side and the cap top. The inspection devices 50, 650, 950 also include a flat, surface-side portion 57, 657, 957 which hangs over the side of the cap top of the hat stringer and travels along the web side of the hat stringer, thereby providing orientation between the hat stringer and the inspection device as a reference and to provide consistency for inspection operations.

The inspection devices, and particularly the sensor holders, define a plurality of sensor recesses 12, 52, 812, 952 by which inspection sensors may be supported and oriented. Typically a plurality of sensors recesses of an inspection device of the present invention may be arranged in an ordered matrix array providing full inspection coverage over the area of the matrix. However, embodiments of the present invention may include various arrangements of sensor recesses designed for different types of inspection applications which do not require an ordered matrix but may use, for example, an arrangement of recesses designed to inspect a specific feature of a structure where the arrangement of recesses corresponds to the shape of the feature. The term matrix is used herein to refer to a two-dimensional (2D) array, and is not limited to an ordered or uniform matrix array. Similarly, inspection sensors may be strategically placed and oriented to provide more thorough inspections, such as aiming transducers at the corners or edges of a hat stiffener. Support structures for inspection sensors, referred to as sensor holders of an inspection device, may be designed and fabricated for specific placement and orientation of inspection sensors corresponding to the intended shape and size of a structure to be inspected. For example, the inspection devices 10, 50, shown in FIGS. 1-4 are designed for inspection of web sides and cap tops of hat stringers and typically would be used with a corresponding matrix array of pulse echo (PE) inspection sensors. The size and orientation of the matrix array of inspection sensors is determined by the intended scan coverage for the particular shape and size of a structure. For example, while the web side inspection device 10 shown in FIGS. 1-4 defines a staggered 3 by 6 matrix of sensor recesses 12 with a bottom corner sensor recess 14, the similar inspection device 610 shown in FIGS. 6 and 7 uses only eleven pulse echo inspection sensors arranged in three staggered rows, two with four sensors each and one with only three sensors. The reduced number of sensors accounts for the short web side 621 of the hat stringer under inspection which does not require use of the entire 3 by 6 integrated matrix. If the web side were taller/wider, more inspection sensors may be included in the sensor matrix for scanning a larger coverage area. If the inspection device includes additional sensor recesses which are not used in a particular application and a fluid couplant is used, sensor plug inserts, such as round rubber stoppers that fill the unused sensor recesses and may be temporarily retained in the recesses by frictional forces and later removed for other scanning operations, may be inserted into the unused sensor recesses to fill and close those recesses and prevent fluid from flowing through those recesses and reducing the pressure and fluid flow around the inspection sensors which are used for inspecting the structure. For ultrasonic inspection, a fluid, like water or air, can be fed through one or more supply lines 650 through a fluid inlet port 86, 652 and into one or more recesses (defined channels, a central cavity, or similar openings that permit the flow of fluid throughout the inspection device) within an inspection device to disperse the fluid between the inspection device, and particularly the inspection sensors supported thereby, and the structure, thereby coupling test signals between the inspection sensors and the structure. This process is known as fluid coupling. Generally an attempt is made to have the fluid flow smoothly between the inspection sensors and the structure without bubbles, cavitation, or turbulence that might detrimentally affect the signal to noise ratio of the ultrasonic inspection signals.

Embodiments of the present invention may be constructed by rapid prototyping as a single part or in multiple parts which are assembled. For example, a single apparatus may be constructed with (i) sensor recesses for supporting a matrix array of pulse echo sensors, (ii) a sensor recess for supporting a pulse echo transducer aligned to inspect a radius feature, (iii) a central cavity through the apparatus, and (iv) a manifold recess for providing fluid flow into the central cavity and thereafter coupling ultrasonic signals of the pulse echo transducers. Alternatively, for example, an apparatus may be constructed with the same or similar features but with a separate manifold structure 38 with a fluid inlet 39 which may be optionally affixed when a fluid couplant is used and used with other inspection apparatus according to the invention. Further, for example, individual pieces of an apparatus may be constructed that can be assembled, such as a surface-side piece 32, a central cavity piece 34, and a cap piece 36, where the central cavity piece 34 is secured between the surface-side piece 32 and the cap piece 36. In such an apparatus, inspection sensors may be secured to the assembled apparatus by having radius portions of the sensors disposed within the central cavity piece 34 and being wider than the radii of the portions of the sensors disposed in and the recesses defined by the surface-side and cap pieces 32, 36. Such a design is further described with reference to FIG. 10. Inspection devices, and particularly sensor holders, of embodiments of the present invention may advantageously be fabricated by rapid prototyping (RP, also known as rapid manufacturing, solid freeform fabrication, computer automated manufacturing, and layered manufacturing). Rapid prototyping involves slicing an electronic design model into electronic layers which are physically built up to create the end product, such as stereolithography which constructs three-dimensional end products from liquid photosensitive polymers (e.g., liquid epoxy or acrylate resin) that solidify when exposed to ultraviolet light (e.g., low-power focused UV laser that traces out each layer). Stereolithography is further described in U.S. Pat. No. 4,575,330 to Hull, assigned to 3D Systems, Inc., of Valencia, Calif. Other types of rapid prototyping are also possible, such as laminated object manufacturing, selective laser sintering, fused deposition modeling, solid ground curing, and 3-D ink-jet printing. Rapid prototyping does not require tooling because the end product is produced directly from an electronic design model, typically a CAD model. Because rapid prototyping does not require tooling, it provides a relatively inexpensive and fast method of manufacturing a custom inspection device. Rapid prototyping is particularly advantageous for custom inspection devices because a CAD model can be created for the particular application corresponding to the structure to be inspected, and a corresponding inspection device can be created. Embodiments of the present invention can be created in relatively little time, for relatively low cost while still being designed specifically for a particular inspection application, even if the structure to be inspected has a unique shape or surface contour.

FIG. 8 is an inspection system of another embodiment of the present invention which includes a rapid prototype sensor holder 820 with a matrix array of recesses 812 for supporting and orienting a plurality of inspection sensors. The sensor holder 820 is formed from four component parts, as described above with reference to FIG. 5, including (i) a cap 821 with sensor recesses for supporting a matrix array of inspection sensors such as pulse echo sensors and, possibly, a sensor recess for supporting an inspection sensor such as a pulse echo sensor aligned to inspect a radius feature; (ii) a central main portion 822 defining a central cavity for dispersing fluid through the central main portion 822 and throughout the entire sensor holder 820; (iii) a bottom cover 823; and (iv) a fluid manifold 824 for providing fluid flow into the central cavity and thereafter coupling ultrasonic signals of the inspection sensors. The embodiment of FIG. 8 also includes a housing 830 for carrying the inspection device and sensor holder thereof. An embodiment of a housing 830 of the present invention advantageously is designed similar to inspection devices to correspond to the shape of the structure to be inspected. For example, the housing 830 of FIG. 8 is designed to slide along a hat stringer while the sensor holder 820 passes over a web side of the hat stringer. The housing 830 may be configured to permit adjustment of the inspection device carried thereby, such as including linear adjustment recesses 834 which permit adjustment of the inspection device with respect to the housing to compensate for hat stringers of different widths. Angle attachments 836 may be connected into these linear adjustment recesses 834, and the inspection device may connect to the angle attachment 836. Angle attachments 836 may also include linear adjustment recesses 838 to which the inspection device is connected. These linear adjustment recesses 834, 836, and similar adjustment mechanisms such as linear mounts 939 shown in FIG. 9, may permit a single housing 830, 930 to be used with different inspection devices and for different sizes and shapes of structures. Similarly, housing features, such as angle attachments 836, may be exchanged for different housing features which correspond to different structure shapes and sizes. For example, different angle attachments may be used for inspecting hat stringers with different angles between the web side of the hat stringer and the skin (or superstructure) of the structure. The housing 830 may include a handle 832 which may advantageously be used by a technician to control the inspection system during manual inspection operations.

In FIG. 8, the inspection system 810 is designed with a flat, surface-side "skin" portion 818 designed for traveling over the structure skin or portion of the hat stringer attached to the structure skin. The inspection system 810 has a convex corner 817 corresponding to the corner of the hat stringer or between the hat stringer and the structure skin and transitioning to a flat, surface-side "web" portion 819. The angle between the skin portion 818 and web portion 819 corresponds to the angle between the skin and the web side of the hat stringer (and the angle of the angle attachments 836) to permit the inspection system 810 to travel over the web side of the hat stringer.

FIG. 9 is an inspection system 950 of another embodiment of the present invention which includes a rapid prototype sensor holder 920 with a matrix array of recesses 952 for supporting and orienting a plurality of ultrasonic sensors. Like the inspection system of FIG. 8, the inspection system 950 of FIG. 9, includes a housing 930 configured to permit adjustment of the inspection device carried thereby, such as including linear adjustment recesses 934, and including a handle 932 for use during manual inspection operations. Because the inspection system 950 is configured to inspect the cap top of a hat stringer, angle attachments are not required. With regard to the configuration of the inspection system 950, the housing 930 is designed with a flat, surface-side "skin" portion 958 for traveling over the cap top of hat stringers. The housing 930 transitions at a concave corner 956, corresponding to the corner of the hat stringer between the web side and the top cap, from the flat, surface-side "skin" portion 958 into a surface-side "web" portion 957. The surface-side "web" portion 957 hangs over the side of the cap top of the hat stringer and travels along the web side of the hat stringer, thereby providing orientation between the hat stringer and the inspection device as a reference and to provide consistency for inspection operations.

The inspection system 950 also includes an optical shaft encoder (OSE) mount piece 984 to which an optical shaft encoder 980 with a wheel 982 are attached. The inspection system 810 of FIG. 8 may also incorporate an optical shaft encoder for recording positional information. For semi-automated or automated scanning operations, the optical shaft encoder 980 and wheel 982 can be used to detect the position and/or motion of the inspection device over the cap top of a hat stringer. The optical shaft encoder mount piece 984 may attach to the rest of the housing 930 along linear adjustment recesses 939 which can be used to adjust the vertical height of the optical shaft encoder mount piece 984 to compensate for inspection of hat stringers of different heights. Other embodiments of the present invention may be similarly designed to permit adjustment for different sizes of other structures. Similarly, other embodiments of the present invention may be used with a drive motor or like automated drive mechanism to move an inspection device along a structure for inspection; alternatively, a magnetically coupled crawler or motion controlled robotic arm may be use used to control movement of an inspection device along a structure for inspection.

Figure 10:
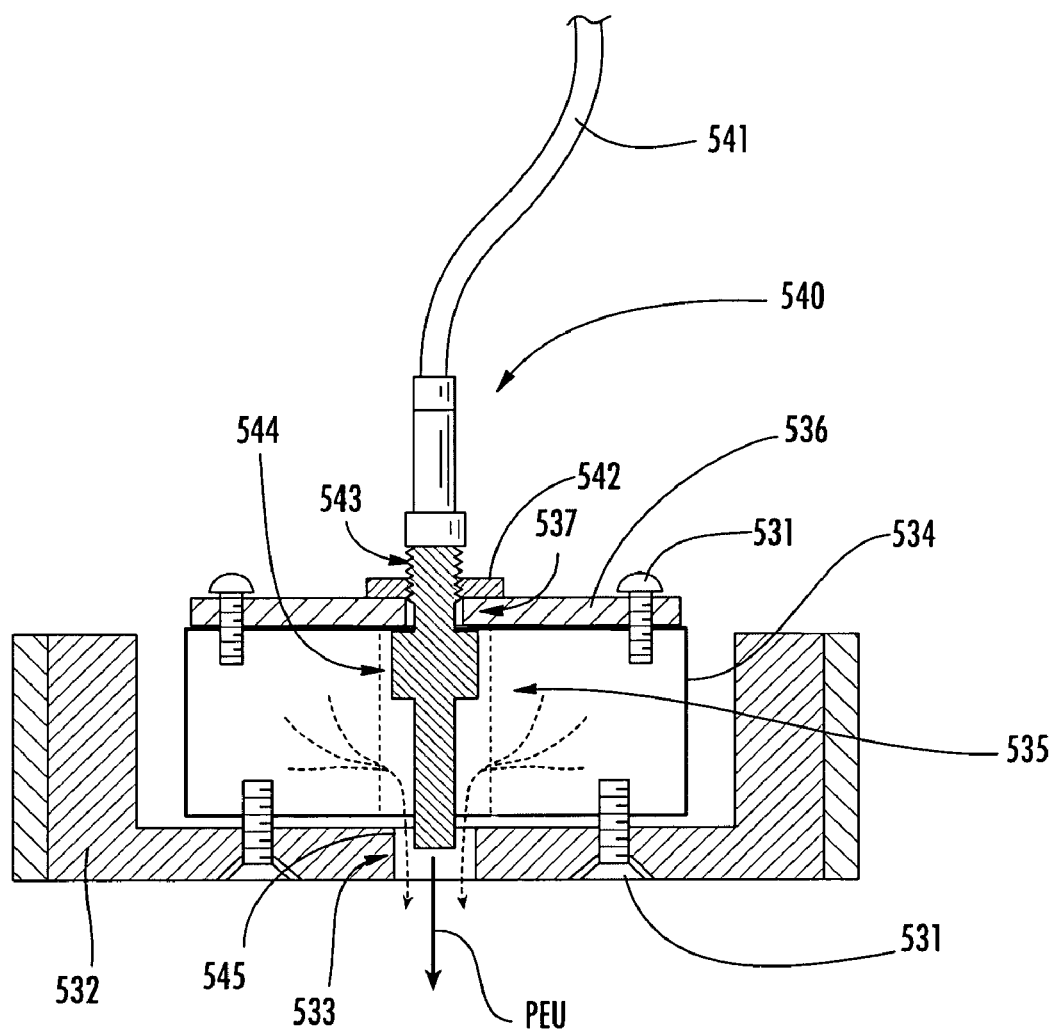
FIG. 10 is a cross-sectional diagram of assembled components of one embodiment of an inspection device of the present invention.

As discussed with reference to FIG. 5, individual pieces of an embodiment of an apparatus of the present invention may be constructed that can then be assembled to create the apparatus. FIG. 10 is a cross-sectional diagram of assembled components of one embodiment of an inspection device of the present invention. The cross-sectional diagram of FIG. 10 is intended merely to depict the manner in which an inspection sensor may be secured within separate component pieces of an embodiment of an apparatus of the present invention. FIG. 10 is depicted with only one inspection sensor and is not intended to represent an embodiment of the present invention with an imbedded matrix of inspection sensors. For example, an inspection sensor 540 is shown supported by and oriented by the support stricture 532, 534, 536. The inspection sensor 540 is configured with a large radius section 544 which is disposed within a recess 535 of the central cavity piece 534 and smaller radius sections 543, 545 which, respectively, protrude through and are disposed in a recess in the cap piece 536 and surface-side piece 532. The smaller radius section 543 protruding through the cap piece 536 may include threads along which a securing nut 542 may rotate to pull the inspection sensor upwards until the large radius section 544 contacts with the smaller radius recess 537 of the cap piece 536, thereby securely supporting and orienting the inspection sensor 540 in the support structure 532, 534, 536 which is fastened together by screws 531. The design of the smaller radius section 545 which is disposed within the recess 535 of the surface-side piece 532 may be influenced by the desire to permit a fluid couplant to pass from a recess 535 of the central cavity piece 534, around the smaller radius section 545, and through the recess of the recess 535 of the surface-side piece 532 to couple ultrasonic signals between the inspection sensor 540 and a structure under inspection.

Also visible in FIG. 10 is the space between the vertical sides of the surface-side piece 532 and the central cavity piece 534. By designing the surface-side piece 532 larger than the central cavity piece 534, different central cavity pieces may be exchanged, while using the same surface-side piece 532, and possibly using the same cap piece 536. Such modular design construction permits an apparatus of the present invention which is composed of various individual pieces to be used with interchangeable pieces for the apparatus. For example, the recesses of two central cavity pieces may be different to support different inspection sensors; similarly, one central cavity piece may include a central cavity through which a fluid couplant can flow while another central cavity piece may be solid except for inspection sensor recesses and used for an inspection application that does not require or cannot permit fluid coupling.

The invention should not be limited to the specific disclosed embodiments and modifications and other embodiments of the invention are intended to be included within the scope of the appended claims. Specific terms are used in a generic and descriptive sense only and not for purposes of limitation.

That which is claimed:

1. A non-destructive inspection apparatus for inspecting a structure, comprising:
    a sensor holder defining a plurality of holes for supporting and orienting a plurality of non-destructive inspection sensors arranged in a matrix array having at least two rows and at least two columns, wherein the sensor holder is configured for traveling over at least a first portion of the structure, and wherein at least a first offset hole in a first row of the matrix array of holes is defined at a first offset position from the holes in other columns in the matrix array of holes, such that the first offset hole is positioned to inspect a different portion of the structure than the holes in other columns in the matrix array of holes.

2. The apparatus of claim 1, wherein the sensor holder is further configured to define the plurality of holes aligned at a first angle to the structure to permit a plurality of non-destructive inspection sensors supported by the plurality of holes aligned at the first angle and arranged in the matrix array to inspect a first portion of the structure at the first angle while the sensor holder travels over at least the first portion of the structure.

3. The apparatus of claim 1, wherein the sensor holder further defines at least one radius hole defined at a second angle to the structure for supporting at least one non-destructive inspection sensor for inspecting at least one radius feature of the structure while the sensor holder travels over at least the first portion of the structure.

4. The apparatus of claim 3, further comprising a plurality of pulse echo ultrasonic inspection sensors connected to the sensor holder and disposed within the holes of the matrix array and the at least one radius hole.

5. The apparatus of claim 1, further comprising a fluid manifold and a fluid inlet port connected to the fluid manifold, wherein the fluid inlet port is configured for injecting a fluid into the fluid manifold, and wherein the sensor holder is further configured for permitting the dispersion of fluid from the fluid manifold throughout the holes of the matrix array.

6. The apparatus of claim 5, further comprising a plurality of pulse echo ultrasonic inspection sensors connected to the sensor holder and disposed within holes of the matrix array, and wherein the sensor holder is further configured for coupling ultrasonic signals of the pulse echo ultrasonic inspection sensors to the structure by passing fluid through the holes and between the pulse echo ultrasonic inspection sensors and the structure.

7. The apparatus of claim 6, further comprising at least one transducer plug insert that is disposed within a hole of the matrix array.

8. The apparatus of claim 1, further comprising a plurality of pulse echo ultrasonic inspection sensors connected to the sensor holder and positioned within the holes of the matrix array.

9. The apparatus of claim 8, further comprising an encoder configured for measuring at least one of the following characteristics of the inspection apparatus with respect to the structure under inspection: position, speed, direction, and velocity.

10. The apparatus of claim 8, further comprising an optical shaft encoder for detecting the position of the sensor holder with respect to the structure.

11. The apparatus of claim 8, further comprising a motor for moving the sensor holder over the structure.

12. The apparatus of claim 1, wherein all of the holes of each row of the matrix array of holes are defined in offset positions from all of the holes of each of the other rows of the matrix array of holes.

13. A system for inspecting a structure comprising:
    a housing configured for traveling over at least a first portion of the structure under inspection;
    a sensor holder carried by the housing, wherein the sensor holder defines a plurality of holes for supporting and orienting a plurality of non-destructive inspection sensors arranged in a matrix array, and wherein the sensor holder is configured for traveling over at least the first portion of the structure under inspection;
    a plurality of non-destructive inspection sensors carried by the sensor holder for inspecting the structure as the sensor holder is moved over the structure, and wherein the plurality of sensors are disposed within holes of the matrix array;
    a fluid manifold and a fluid inlet port connected to the fluid manifold, wherein the fluid inlet port is configured for injecting a fluid into the fluid manifold, and wherein the sensor holder is further configured for permitting the disbursement of fluid from the fluid manifold throughout the holes of the matrix array.

14. The system of claim 13, wherein the sensor holder defines the fluid manifold.

15. The system of claim 13, further comprising a motor carried by the housing and configured to move the housing over at least the first portion of the structure.

16. The system of claim 15, wherein the housing and sensor holder are configured for inspecting hat stringers, and wherein the housing is further configured for adjusting the position of the motor carried by the housing for inspecting hat stringers with different heights.

17. The system of claim 13, further comprising an encoder carried by the housing and configured for measuring at least one of the following characteristics of the housing with respect to the structure under inspection: position, speed, direction, and velocity.

18. The system of claim 17, wherein the housing is further configured for adjusting the position of the sensor holder carried by the housing to position the matrix array of sensors for inspecting the structure.

19. The system of claim 13, wherein the housing is further configured to define a handle for manual inspection of a structure.

20. A non-destructive inspection apparatus for inspecting a structure, comprising:

a sensor holder defining a plurality of holes for supporting and orienting a plurality of non-destructive inspection sensors arranged in a matrix array, wherein the sensor holder is configured for traveling over at least a first portion of the structure, and wherein the sensor holder is further configured to define at least a first hole of the plurality of holes aligned at a first angle to the structure to permit a first one of the plurality of non-destructive inspection sensors supported by the first holes and aligned at the first angle to inspect at least a portion of the structure at the first angle while the sensor holder travels over the structure.

21. The apparatus of claim 20, wherein the sensor holder is further configured to define the plurality of holes aligned at the first angle to the structure to permit a plurality of non-destructive inspection sensors supported by the plurality of holes aligned at the first angle and arranged in the matrix array to inspect a planar portion of the first portion of the structure at the first angle while the sensor holder travels over at least the first portion of the structure.

22. The apparatus of claim 20, further comprising a fluid manifold and a fluid inlet port connected to the fluid manifold, wherein the fluid inlet port is configured for injecting a fluid into the fluid manifold, and wherein the sensor holder is further configured for permitting the dispersion of fluid from the fluid manifold throughout the holes of the matrix array.

23. The apparatus of claim 22, further comprising a plurality of pulse echo ultrasonic inspection sensors connected to the sensor holder and disposed within holes of the matrix array, and wherein the sensor holder is further configured for coupling ultrasonic signals of the pulse echo ultrasonic inspection sensors to the structure by passing fluid through the holes and between the pulse echo ultrasonic inspection sensors and the structure.

24. A non-destructive inspection apparatus for inspecting a structure, comprising:

a sensor holder defining a plurality of holes for supporting and orienting a plurality of non-destructive inspection sensors arranged in a matrix array, wherein the sensor holder is configured for traveling over at least a first portion of the structure, and wherein the sensor holder further defines at least one radius hole defined at a second angle to the structure for supporting at least one non-destructive inspection sensor for inspecting at least one radius feature of the structure while the sensor holder travels over at least the first portion of the structure.

25. The apparatus of claim 24, further comprising a plurality of pulse echo ultrasonic inspection sensors connected to the sensor holder and disposed within the holes of the matrix array and the at least one radius hole.

26. The apparatus of claim 24, further comprising a fluid manifold and a fluid inlet port connected to the fluid manifold, wherein the fluid inlet port is configured for injecting a fluid into the fluid manifold, and wherein the sensor holder is further configured for permitting the dispersion of fluid from the fluid manifold throughout the holes of the matrix array.

27. The apparatus of claim 26, further comprising a plurality of pulse echo ultrasonic inspection sensors connected to the sensor holder and disposed within holes of the matrix array, and wherein the sensor holder is further configured for coupling ultrasonic signals of the pulse echo ultrasonic inspection sensors to the structure by passing fluid through the holes and between the pulse echo ultrasonic inspection sensors and the structure.

\* \* \* \* \*